United States Patent
Iwata

(10) Patent No.: US 9,694,207 B2
(45) Date of Patent: Jul. 4, 2017

(54) CONTROL DEVICE FOR SCANNING ELECTROMAGNET AND PARTICLE BEAM THERAPY APAPRATUS

(75) Inventor: Takaaki Iwata, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 349 days.

(21) Appl. No.: 14/399,099

(22) PCT Filed: Aug. 21, 2012

(86) PCT No.: PCT/JP2012/071046
§ 371 (c)(1),
(2), (4) Date: Nov. 5, 2014

(87) PCT Pub. No.: WO2014/030207
PCT Pub. Date: Feb. 27, 2014

(65) Prior Publication Data
US 2015/0126798 A1    May 7, 2015

(51) Int. Cl.
*A61N 5/10* (2006.01)

(52) U.S. Cl.
CPC ........... *A61N 5/1067* (2013.01); *A61N 5/103* (2013.01); *A61N 5/1043* (2013.01);
(Continued)

(58) Field of Classification Search
CPC ........ A61N 5/10; A61N 5/103; A61N 5/1043; A61N 5/1048; A61N 5/1067;
(Continued)

(56) References Cited

U.S. PATENT DOCUMENTS 5,585,642 A    12/1996    Britton et al.
5,895,926 A    4/1999    Britton et al.
(Continued)

FOREIGN PATENT DOCUMENTS

DE    36 43 893 A1    6/1988
EP    2 305 351 A1    4/2011
(Continued)

OTHER PUBLICATIONS

The extended European Search Report issued on Mar. 15, 2016, by the European Patent Office in corresponding European Patent Application No. 12883195.5-1666. (7 pages).
(Continued)

*Primary Examiner* — Charles A Marmor, II
*Assistant Examiner* — Thaddeus Cox
(74) *Attorney, Agent, or Firm* — Buchanan Ingersoll & Rooney PC

(57) ABSTRACT

A control device (control unit) to be used for controlling a scanning electromagnet that is used for scanning irradiation, which includes: a command-value processing line (a memory, an arithmetic circuit, an interface) that generates a command value for driving the scanning electromagnet on the basis of a treatment plan, and outputs the generated command value in synchronization with an accelerator; and a comparator unit that detects an error in the processing line; wherein a circuit (for example, the arithmetic circuit) that constitutes at least a part of the processing line is made redundant, and the comparator unit detects occurrence of the error in the processing line when outputs from the circuit made redundant are unmatched to each other.

16 Claims, 9 Drawing Sheets

(52) U.S. Cl.
CPC ......... *A61N 5/1048* (2013.01); *A61N 5/1077* (2013.01); *A61N 2005/1074* (2013.01); *A61N 2005/1087* (2013.01)

(58) Field of Classification Search
CPC .......... A61N 5/1077; A61N 2005/1074; A61N 2005/1087; A61N 2005/1092
See application file for complete search history.

(56) References Cited

U.S. PATENT DOCUMENTS

| | | | |
|---|---|---|---|
| 6,268,610 | B1 | 7/2001 | Pu |
| 6,509,573 | B1 | 1/2003 | Badura et al. |
| 2003/0229836 | A1 | 12/2003 | Matsumoto |
| 2007/0033511 | A1* | 2/2007 | Davies ................ G06F 11/1675 714/799 |
| 2011/0073778 | A1 | 3/2011 | Natori et al. |
| 2012/0305790 | A1 | 12/2012 | Hanawa et al. |
| 2013/0026388 | A1 | 1/2013 | Claereboudt et al. |

FOREIGN PATENT DOCUMENTS

| | | |
|---|---|---|
| JP | 05-094381 A | 4/1993 |
| JP | 5-94381 A | 4/1993 |
| JP | 06-329042 A | 11/1994 |
| JP | 6-329042 A | 11/1994 |
| JP | 08-241217 A | 9/1996 |
| JP | 11-114078 A | 4/1999 |
| JP | 2001-212253 A | 8/2001 |
| JP | 2003-316599 A | 11/2003 |
| JP | 2005-296162 A | 10/2005 |
| JP | 2008-237687 A | 10/2008 |
| JP | 2008-299767 A | 12/2008 |
| JP | 2011-072537 A | 4/2011 |
| JP | 2011-161055 A | 8/2011 |
| WO | 96/25201 A1 | 8/1996 |
| WO | 2011/121037 A1 | 10/2011 |

OTHER PUBLICATIONS

Office Action issued on Jun. 22, 2016, by the Chinese Patent Office in corresponding Chinese Patent Application No. 201280075353.7, and an English Translation of the Office Action. (12 pages).

Office Action issued on May 19, 2015, by the Taiwanese Patent Office in corresponding Taiwanese Patent Application No. 101149717, and an English Translation of the Office Action. (10 pages).

Office Action issued on Nov. 11, 2014, by the Japanese Patent Office in corresponding Japanese Patent Application No. 2014-531405, and an English Translation of the Office Action. (6 pages).

International Search Report (PCT/ISA/210) mailed on Nov. 27, 2012, by the Japanese Patent Office as the International Searching Authority for International Application No. PCT/JP2012/071046.

* cited by examiner

(12) United States Patent

CONTROL DEVICE FOR SCANNING ELECTROMAGNET AND PARTICLE BEAM THERAPY APAPRATUS

TECHNICAL FIELD

The present invention relates to a control device for scanning electromagnet to be used in a particle beam therapy apparatus used for cancer treatment or the like, in particular, in a particle beam therapy apparatus of a scanning irradiation type, and a particle beam therapy apparatus using the same.

BACKGROUND ART

A particle beam therapy is given for treating a diseased site as a treatment target by irradiating it with a beam of charged particles (particle beam) to thereby damage a tissue of the diseased site. At that time, in order not to cause damage to the surrounding tissue so that a sufficient dose is imparted to the tissue of the diseased site, it is required to adequately control the quantity of radiation and the region of irradiation (irradiation field). As methods of controlling the irradiation field, there are those of a conventionally-used broad-beam irradiation type in which the irradiation field is formed by beam transmission through a physical limiter, and those of a scanning irradiation type which have been recently focused on and in which the irradiation field is directly formed by scanning (referred to, for example, in Patent Documents 1 to 3). In particular, in the case of the scanning irradiation type, an in-plane dose distribution can also be controlled freely, thus making it possible to impart a dose matched to a state of the diseased site.

In any of these cases, a controller for controlling en electromagnet is likely to cause its failure, because it is being placed in an environment where many neutrons, etc., are produced in order to control a trajectory of the particle beam and the region of irradiation. Accordingly, as shown in Patent Documents 4 to 7, it is conceivable to make redundant a line of the controller to thereby detect the failure.

CITATION LIST

Patent Document

Patent Document 1: Japanese Patent Application Laid-open No. H11-114078 (paragraphs 0026 to 0039, FIG. 1 to FIG. 4)
Patent Document 2: Japanese Patent Application Laid-open No. 2001-212253 (paragraphs 0052 to 0055, FIG. 1)
Patent Document 3: Japanese Patent Application Laid-open No. 2005-296162 (paragraphs 0023 to 0038, FIG. 1 to FIG. 4, paragraphs 0039 to 0045, FIG. 5)
Patent Document 4: Japanese Patent Application Laid-open No. H05-94381 (paragraph 0007, FIG. 1)
Patent Document 5: Japanese Patent Application Laid-open No. H08-241217 (paragraphs 0025 to 0026, FIG. 1)
Patent Document 6: Japanese Patent Application Laid-open No. 2003-316599 (paragraphs 0015 to 0019, FIG. 1)
Patent Document 7: Japanese Patent Application Laid-open No. 2008-299767 (paragraphs 0008 to 0016, FIG. 1, FIG. 2)

SUMMARY OF THE INVENTION

Problems to be Solved by the Invention

However, in the above documents, no specific description is given as to what line should be made redundant with respect to the particle beam therapy apparatus. Meanwhile, a system of the particle beam therapy apparatus is huge, so that many controllers are required even only under the environment where neutrons, etc., are produced. Thus, it is not realistic to make all of these controllers redundant. Accordingly, the inventor of the present invention has studied about an influence of the failure on the particle beam therapy apparatus. As a result, it has been now found that, in particular, a command-value processing line in the particle beam therapy apparatus of a scanning irradiation type is a highest priority target for which a measure should be taken against its failure.

For example, in the case of the broad-beam irradiation type, an electromagnet for scanning the particle beam (wobbler electromagnet) is used for enlarging the region of irradiation to thereby fully cover a transmission shape of the physical limiter, and at the downstream thereof, a scatterer for scattering the particle beam is placed. Thus, even if a failure occurs in the line of controlling the wobbler electromagnet so as to make it unable to control the particle beam, the beam is scattered by the downstream scatterer. Accordingly, the concentration degree of dose is low, and thus an influence on a patient by an over dose (excessive dose) in the case of occurrence of the failure, is not so serious matter.

Meanwhile, in the case of the scanning irradiation type, an electromagnet for scanning the particle beam (scanning electromagnet) scans a narrow particle beam, which is referred to as a pencil beam, to thereby directly form the irradiation field. Thus, the particle beam that becomes uncontrollable due to occurrence of the failure in the line of controlling the scanning electromagnet is radiated directly toward the patient. Accordingly, in the case of the scanning irradiation type, an influence on the patient by an excessive dose at the time of the failure in the irradiation-related controller is more serious as compared to the case of the broad-beam irradiation type.

Moreover, in the case of the scanning irradiation type, even if the scanning electromagnet is controlled just according to the command value, when an error occurs in the command value itself, a serious influence arises similarly to when the electromagnet fails. Thus, even when a displacement between the command value and the position of the actual particle beam is made detectable by providing a monitor for measuring the position of the particle beam as described, for example, in Patent Document 7, it is unable to avoid the influence on the patient by an excessive dose.

The present invention has been made to solve the problem as described above, and an object thereof is to suppress the influence by an excessive dose, to thereby enable a particle beam therapy that is capable of imparting an adequate dose.

Means for Solving the Problems

A control device for scanning electromagnet of the invention is a control device for scanning electromagnet to be used for controlling a scanning electromagnet that is used for scanning irradiation so as to form a particle beam supplied from an accelerator into an irradiation field matched to a treatment plan, said control device for scanning electromagnet characterized by comprising: a command-value processing unit that generates a command value for driving the scanning electromagnet on the basis of the treatment plan, and outputs the generated command value in synchronization with the accelerator; and an error detection unit that detects a processing error in the command-value processing unit; wherein a circuit that constitutes at least a part of the command-value processing unit is made redundant, and the error detection unit detects occurrence of the processing error when outputs from the circuit made redundant are unmatched to each other.

Effect of the Invention

According to the control device for scanning electromagnet and the particle therapy apparatus of the invention, since an error in processing the command value for performing scanning can be promptly detected, an excessive dose due to concentration of dose can be suppressed, so that it is possible to perform a particle beam therapy capable of imparting an adequate dose.

MODES FOR CARRYING OUT THE INVENTION

Embodiment 1

Figure 1:
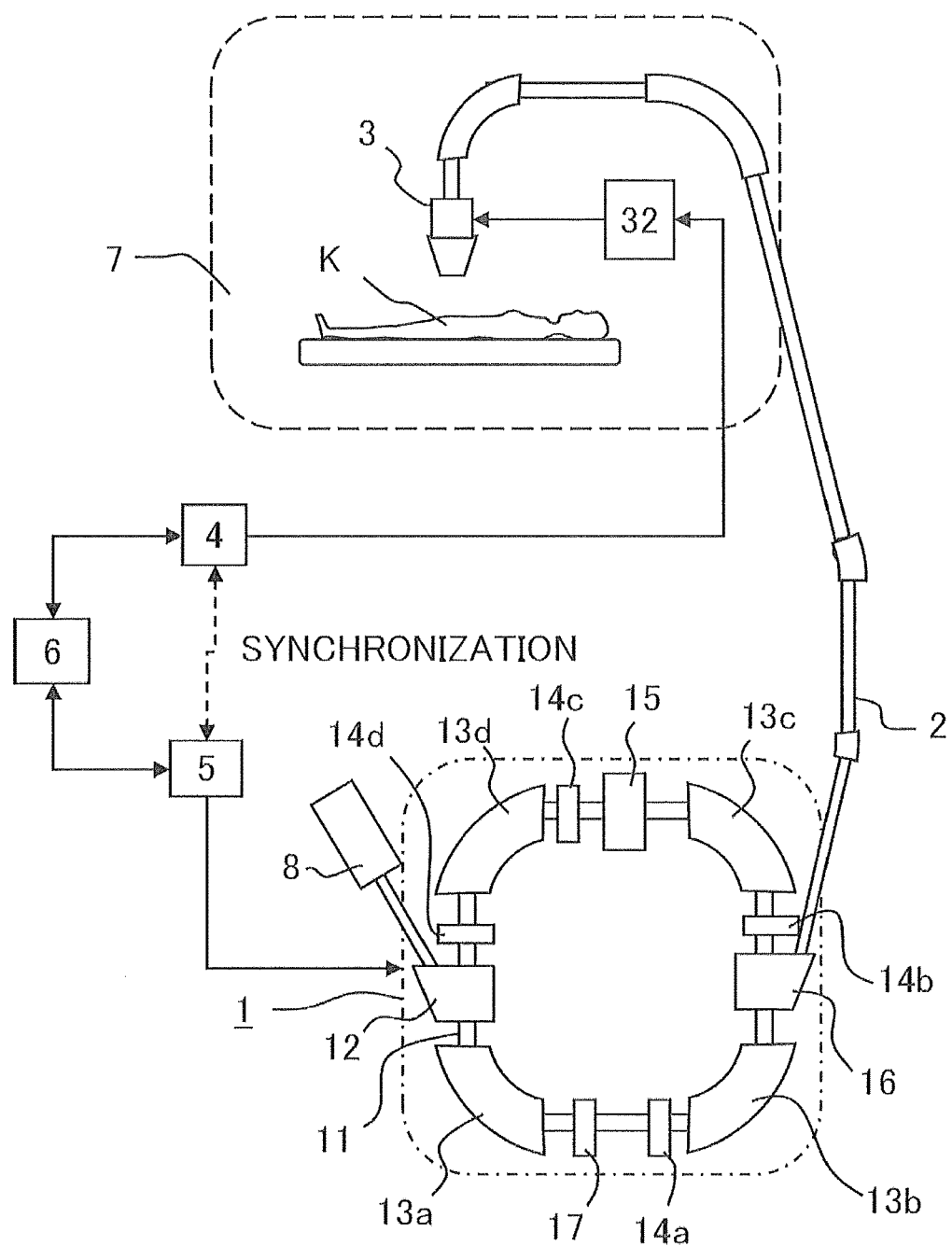
FIG. 1 is a diagram for illustrating a configuration of a particle beam therapy apparatus according to Embodiment 1 of the invention.
Figure 2:
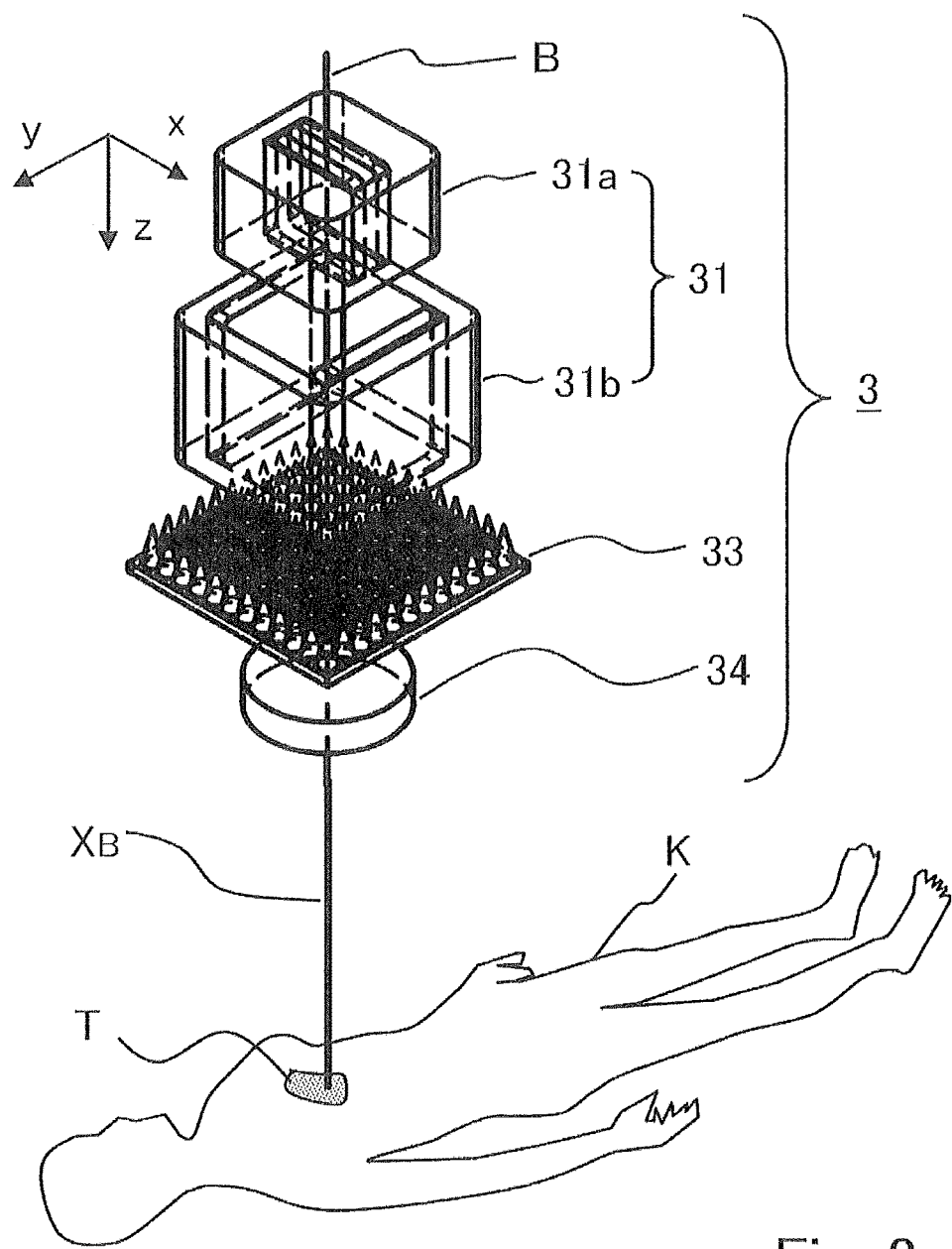
FIG. 2 is a diagram for illustrating a configuration of an irradiation device in the particle beam therapy apparatus according to Embodiment 1 of the invention.
Figure 3:
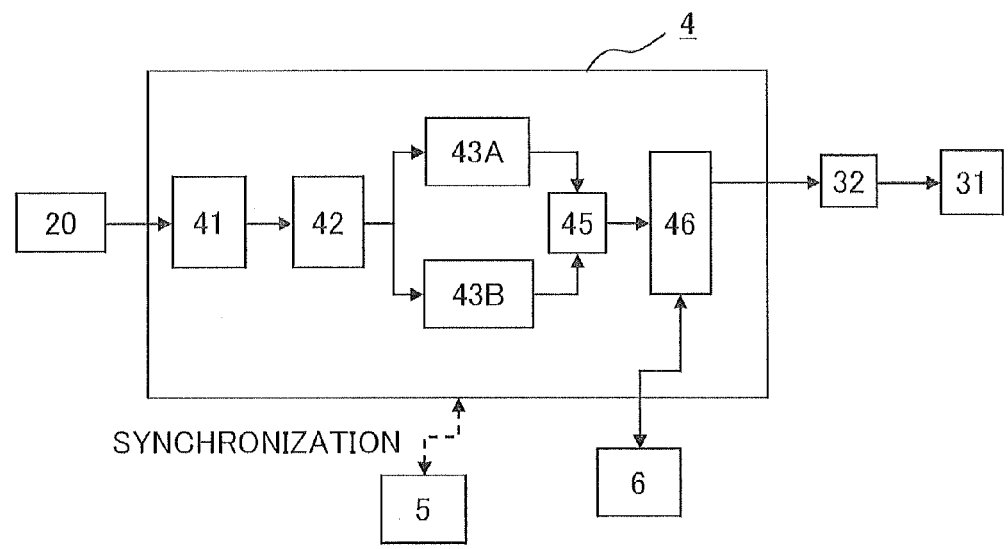
FIG. 3 is a block diagram for illustrating a configuration of a control device for scanning electromagnet in the particle beam therapy apparatus according to Embodiment 1 of the invention.

Hereinafter, a configuration of a particle beam therapy apparatus according to Embodiment 1 of the invention will be described. FIG. 1 to FIG. 3 are given for illustrating a configuration of the particle beam therapy apparatus according to Embodiment 1 of the invention, in which FIG. 1 is a diagram for illustrating an overall configuration of the particle beam therapy apparatus, FIG. 2 is a diagram showing a configuration of an irradiation device in the particle beam therapy apparatus, and FIG. 3 is a brook diagram showing a configuration of a controller (control unit) that controls a scanning electromagnet.

The particle beam therapy apparatus 1 according to Embodiment 1 of the invention is characterized in the configuration of the control device that controls a scanning electromagnet for performing scanning irradiation. Specifically, a processing line of a command value for driving the scanning electromagnet is made redundant, so that a failure is detected by comparing outputs from a plurality of redundant processing lines, depending on whether or not the outputs are matched to each other. Notwithstanding, prior to the description of a configuration and operation for detecting the failure, a general configuration of the particle beam therapy apparatus 1 will be described using FIG. 1.

In the figure, the particle beam therapy apparatus 1 includes, as a source of supplying a particle beam, a circular accelerator 10 which is a cyclotron (hereinafter, referred to simply as "accelerator"); an irradiation device 3 provided in each of treatment rooms 7; a transport system 2 that connects between the accelerator 10 and the irradiation device 3 so as to transport the particle beam from the accelerator 10 to the irradiation device 3 of each treatment room 7; and a control system that controls each portion. Note that, in the figure, for simplification's sake, only one treatment room and one irradiation device 3 are shown among the plurally-provided treatment rooms and irradiation devices. Further, the control system includes a main controller that controls the whole of the particle beam therapy apparatus 1 and a plurality of local controller individually provided for the respective systems; however, among these, there are only shown a control unit 5 that is a local controller of the accelerator 10, a control unit 4 that is a local controller of the irradiation device 3 and a main control unit 6 that is a main controller for controlling the whole of the particle beam therapy apparatus 1 in a cooperative manner. Next, description will be turned to the respective configurations.

The accelerator 10 includes a vacuum duct 11 that provides a trajectory channel for causing the charged particles to go around therethrough; an injection device 12 for injecting the charged particles supplied from a pre-accelerator 8 into the vacuum duct 11; bending electromagnets 13a, 13b, 13c, 13d (referred to collectively as numeral 13) for bending a trajectory of the charged particles so that the charged particles go around along the round trajectory in the vacuum duct 11; convergence electromagnets 14a, 14h, 14c, 14d (referred to collectively as numeral 14) that cause the charged particles in the round trajectory to converge so as not to diverge; a high-frequency acceleration cavity 15 that applies to the charged particles going around, a high frequency voltage synchronous with the particles to thereby accelerate the particles; an emission device 16 for taking out from the accelerator 10 the charged particles accelerated in the accelerator 10 as a particle beam having a predetermined energy, so as to emit it toward the transport system 2; and a sextupole magnet 17 that excites resonance in the round trajectory for emitting the particle beam from the emission device 16.

It is noted that, there are provided not-shown devices for controlling the respective parts, such as, for the bending electromagnets 13, a bending electromagnet control device that controls currents for exciting the bending electromagnets 13, and for the high-frequency acceleration cavity 15, a high frequency source for supplying the high frequency voltage to the high-frequency acceleration cavity 15 and a high-frequency control device for controlling the high frequency source. There is further provided in the control unit 5, a controller or the like that controls the whole of the accelerator 10 by controlling the bending electromagnet control device, the high-frequency control device, the convergence electromagnets 14 and like other components.

Further, although the pre-accelerator 8 is illustrated as a single device in the figure for simplification's sake, it is actually provided with an ion source (ion beam generating device) for generating charged particles (ions) of proton, carbon (heavy particle) or the like, and a linear accelerator system that initially accelerates the generated charged particles. Here, the charged particles that have entered the accelerator 10 from the pre-accelerator 8 are accelerated by a high frequency electric field up to approx. 70% to 80% of the light velocity while being bent by the magnets.

The particle beam accelerated by and emitted from the accelerator 10 is emitted to the transport system 2 called as HEBT (High Energy Beam Transport) system. The transport system 2 includes a vacuum duct that provides a transport channel of the particle beam; a switching electromagnet that is a switching device for switching the beam trajectory of the particle beam; and a bending electromagnet that bends the particle beam by a predetermined angle. Note that, in the figure, only one irradiation device is shown as described above and thus the switching electromagnet, etc., is not illustrated; however, by switching the trajectory as necessary by means of the switching electromagnet, it is possible to supply the particle beam emitted from the single accelerator 10 to the irradiation device of any of the treatment rooms.

The irradiation device 3 is a device that irradiates a diseased site with the particle beam supplied from the transport system 2 after forming the beam into an irradiation field according to the size and depth of an irradiation target. As shown in FIG. 2, the irradiation device 3 includes a scanning electromagnet 31 that deflects the so-called pencil-like particle beam supplied from the accelerator 10 through the transport system 2 in a given direction in a plane nearly perpendicular to a beam axis $X_B$; a ridge filter 33 for spreading the width of the Bragg peak according to the thickness of the irradiation target T; and a range shifter 34 that changes the energy (range) of the particle beam according to the deepness of the irradiation target (irradiation depth).

The scanning electromagnet 31 is configured by placing along the beam axis $X_B$, a unidirectional scanning electromagnet 31a and a unidirectional scanning electromagnet 31b each being for performing scanning in one dimension in a plane (x-y) perpendicular to the beam axis $X_B$ so that their deflection directions are different to each other (for example, in the figure, orthogonal x-direction and y-direction). By adjusting the amount of excitation of each of the unidirectional scanning electromagnets 31a, 31b, it is possible to deflect the incident particle beam in a predetermined direction relative to the beam axis $X_B$; so that the particle beam is emitted toward a predetermined location in the x-y plane of the diseased site T as the irradiation target.

The ridge filter 33 is formed, for example, of a number of cone-like objects or cross-sectionally triangle plates that are arranged in a direction of the plane, so that if a particle-beam passing plane is assumed to be divided into many small regions, there are portions of the particle beam each passing through different thicknesses in each small region. In the figure, for ease of understanding, it is illustrated as circular cones arranged in the plane. This makes the Bragg peak to be spread, so that the particle beam becomes to have a so-called SOBP (Spread-Out Bragg Peak). That is, by means of the ridge filter 33, the width in a depth direction to which dose can be imparted is enlarged. The range shifter 34 is given for attenuating the energy of the incident particle beam by a predetermined amount, which includes a plurality of resin plate members having predetermined thicknesses, for example, so that the attenuation amount can be specified according to the combination (total thickness) of the plate members.

Namely, in the case where the diseased site T is irradiated using a scanning irradiation method, the irradiation field corresponding to a shape of the diseased site T in a direction parallel to the beam axis $X_B$, i.e. in a depth(z) direction, is formed by the above-described ridge filter 33 and range shifter 34. Further, the irradiation field corresponding to a shape of the diseased site T in a direction parallel to a plane (x-y) perpendicular to the beam axis $X_B$ is formed by the scanning electromagnet 31. At that time, the two-dimensional irradiation field in a direction in the plane (x-y) is basically formed by changing the combination of deflection angles of the two unidirectional scanning electromagnets 31a, 31b in a state where the depth-direction irradiation field is determined.

These deflection angles are determined depending on intensities of the magnetic fields produced according to currents flowing through the scanning electromagnets (31a, 31b), respectively. Besides, the respective currents are determined by command values output to a driving power source 32 that is provided corresponding to the respective unidirectional scanning electromagnets 31a,31b (although there are actually a driving power source 32a for the electromagnet 31a and a driving power source 32b for the electromagnet 31b, these are collectively represented by numeral 32). Further, the command values are calculated based on coordinate data of the irradiation target stored in a treatment plan device.

And, the particle beam therapy apparatus 1 according to Embodiment 1 of the invention is characterized in the control unit 4 that is the controller of the scanning electromagnet 31 for performing scanning, among the local controllers of the irradiation device 3 of a scanning irradiation type. Namely, with respect to a circuit that performs processing of the command value in the control unit 4, such as, conversion (generation) from coordinate data of the irradiation target into the command value, adjustment of an output timing so as to output the generated command value in synchronization with the accelerator 10, and the like, at least a part of the circuit is made redundant, so that whether or not an error is present in the processing is determined depending on whether or not the respective outputs from the redundant circuits are matched to each other. Next, its detail will be described.

As shown in FIG. 3, the control unit 4 has an interface 41 that functions as a data receiving unit for receiving treatment plan data prepared in a treatment plan device 20, and a memory 42 for storing the treatment plan data received by the interface 41. Here, an arithmetic circuit 43 that performs calculation for converting the treatment plan data (its dimension is defined by the irradiated position and the irradiation dose at, that position) output from the memory 42 into the command value (its dimension is defined by the current and the time) for the scanning electromagnet 31 (or its driving power source 32), is configured so that it is made redundant with a first arithmetic circuit 43A and a second arithmetic circuit 43B that perform the same calculation (processing).

The respective command values calculated by the redundant first arithmetic circuit 43A and second arithmetic circuit 43B are output to a comparator unit 45. The comparator unit 45 compares a calculation result (command value) output from the first arithmetic circuit 43A and a calculation result (command value) output from the second arithmetic circuit 43B. Then, in the case where the thus-compared respective calculation results (command values) are matched to each other, the command value is output, and in the case where the calculation results (command values) are unmatched to each other, a signal indicative of that case (error-occurrence trigger signal) is output, to an interface 46 that functions as a command value transmitting unit. Namely, the comparator unit 45 functions as an error detection unit that detects whether or not an error occurred in either one of the redundant command-value processing lines.

When the command value is output to the interface 46, the interface 46 outputs the command value in synchronization with the accelerator 10 (or its control unit 5) to the driving power source 32, and the driving power source 32 drives the scanning electromagnet 31 on the basis of the output command value. On the other hand, when the error-occurrence trigger signal is output to the interface 46, the interface 46 outputs the error-occurrence trigger signal to the main control unit 6. Namely, the interface 46 functions as a timing adjustment unit that outputs the command value in synchronization with the accelerator 10 and as an error notification unit that notifies another controller, etc., of occurrence of an error when the error occurred in the command-value processing line.

When the error-occurrence trigger signal is output to the main control unit 6, the main control unit 6 outputs a signal for causing the respective systems to display an alarm indication showing the occurrence of the error, or a signal for suspending the particle beam, to the corresponding controllers (for example, the control units 4 and 5).

When the control unit 4 with the configuration as describe above is used as the controller related to the irradiation device 3, an error can be detected on a real-time basis when the error occurred in either one of the redundant arithmetic circuits 43A, 43B, so that it becomes possible to immediately suspend the particle beam so as to prevent an excessive dose. At this time, if a displacement of the irradiation position of the particle beam from its command value is made detectable as described in Patent Document 7, it is unable to detect that an error occurred in the command value itself. Thus, if the command value remains unchanged at a single value, for example, the irradiation is made with a narrow particle beam called as a pencil beam as focusing on a single point, to thereby cause a seriously excessive dose. This arises even when the command value is zero.

In the case of commonly used controls, by setting a command value to zero at the time of failure, safety can be ensured to thereby afford failsafe in many cases. But, if this is applied to a particle beam therapy apparatus of a scanning irradiation type, the particle beam continues to be radiated to a target center called as an isocenter at the time of failure, thus causing a serious situation rather than acting toward the safe side. However, according to the particle beam therapy apparatus 1 according to this embodiment, whether or not an error occurred in the command value processing can be promptly detected solely by making redundant the processing line of the command value of the driving power source 32 for the scanning electromagnet 31. Thus, it becomes possible to suppress the influence by an excessive dose without complicating the apparatus, to thereby impart an optimum dose.

It is noted that, as described above, the scanning electromagnet 31 is configured with two unidirectional electromagnets of the x-direction unidirectional scanning electromagnet 31a and the y-direction unidirectional scanning electromagnet 31b, and thus the command value is calculated for each of the unidirectional scanning electromagnets 31a, 31b. Accordingly, it is desirable to make separately redundant the circuit that calculates the command value of the driving power source 32a for the x-direction unidirectional scanning electromagnet 31a and the circuit that calculates the command value of the driving power source 32b for the y-direction unidirectional scanning electromagnet 31b.

However, the effect emerges even if at least one of them is made redundant. In this case, if a pattern of the command values is known such that one of the command values varies continuously whereas the other of the command values varies intermittently, for example, it is desirable to make redundant preferentially the circuit at the side where the command value varies continuously.

Further, as shown in FIG. 1 and FIG. 3, the control unit 4 has a function of preforming control related to the irradiation device 3 in synchronization with the control unit 5 related to the accelerator 10 in which the particle beam is accelerated and transported. It is also conceivable that a single controller performs functions of the controller related to the irradiation device 3 and the controller related to the accelerator 10; however, it is general to take such distributed cooperative control. In this case, as a control system for the system including a plurality of subsystems (the accelerator 10, the transport system 2, the irradiation device 3 for every treatment room, etc.), a hierarchical control system is used in many cases that comprises local controllers each for exclusively controlling each of the subsystems and a main controller for supervising and controlling the whole thereof. In the particle beam therapy apparatus according to Embodiment 1 of the invention, such a configuration with the main controller and the local controllers is introduced. And, the functions in the control system are divided such that operations controllable in the subsystems are controlled in the local controllers and an operation for controlling the plurality of the systems in their cooperative manner is controlled by the main controller.

Meanwhile, in the particle beam therapy device, generally, a work station or a computer is used as the control system. Thus, respective functions as the main controller and the local controllers are to be implemented by software etc., and therefore, they do not necessarily fall in specific hardware. For example, in FIG. 1 mentioned above and block diagrams described later, the control units 4, 5, 6 are illustrated as if they are individual hardware; however, such illustration is made only for convenience of explanation, and does not reflect their actual conditions. Notwithstanding, depending on an embodiment described later (in particular, Embodiment 3), there is a case, for example, where the controllers (or circuit parts) are distinguished in their physical positions by taking into consideration a position-dependent influence by noise, etc.

As describe above, according to the control device for scanning electromagnet (control unit 4) according to Embodiment 1, there is provided a control device for scanning electromagnet (control unit 4) to be used for controlling the scanning electromagnet 31 that is used for scanning irradiation so as to form the particle beam supplied from the accelerator 10 into an irradiation field matched to a treatment plan, said control device for scanning electromagnet being configured to include: the memory 42, the arithmetic circuit 43 and the interface 46 that function as a command-value processing unit that generates a command value for driving the scanning electromagnet 31 on the basis of the treatment plan (or its data), and outputs the generated command value while adjusting its timing to be in synchronization with the accelerator 10; and the error detection unit (comparator unit 45) that detects a processing error in the command-value processing unit; wherein a circuit (arithmetic circuit 43) that constitutes at least a part of the command-value processing unit is made redundant (as arithmetic circuits 43A, 43B), and the error detection unit (comparator unit 45) detects occurrence of the processing error when outputs from the circuit made redundant are unmatched to each other. Thus, when an error occurred in the command value processing, it is possible to detect it promptly. This makes it possible to suppress an excessive dose from occurring, for example, due to concentration of dose caused by the irradiation position staying unchanged or due to false radiation to a site that should never be irradiated, to thereby perform a particle beam therapy that is capable of imparting an optimum dose.

In particular, as redundant circuits, the arithmetic circuits 43A, 43B are provided that convert the treatment plan data to the command value, so that an error in the processing of generating the command value can be promptly detected.

Further, according to the particle beam therapy apparatus 1 according to Embodiment 1, it is configured to include: the accelerator 10 that supplies a particle beam; the irradiation device 3 that includes the scanning electromagnet 31 for scanning irradiation and performs scanning irradiation matched to a shape of a diseased site using the particle beam supplied from the accelerator 10; the above-described control device for scanning electromagnet (control unit 4) that controls the scanning electromagnet 31; and the cooperation control device (control unit 6) that controls the accelerator 10 and the irradiation device 3 in their cooperative manner; wherein, when the error detection unit (comparator unit 45) detects a processing error, the control device for scanning electromagnet (control unit 4) outputs an error-occurrence signal indicative of occurrence of the processing error to the cooperation control device (control device 6); and wherein, when the error-occurrence signal is output, the cooperation control device (control device 6), suspends at least one of the supply of the particle beam by the accelerator 10 and the irradiation with the particle beam by the irradiation device 3. Thus, it is possible to suppress an excessive dose from occurring due to concentration of dose caused by the irradiation position staying unchanged or due to false radiation to a site that should never be irradiated, to thereby perform a particle beam therapy that is capable of imparting an optimum dose.

Embodiment 2

In Embodiment 1, there have been shown a situation where the conversion from the treatment plan data calculated by the external treatment plan device to the command value for the scanning electromagnet (or its driving power source) is performed by the command-value processing unit that is made redundant in the controller related to the irradiation device. This is because the conversion from the treatment plan data to the command value is dependent on the property of each electromagnet, so that it is natural to cause the controller that is given as a pair with the electromagnet to perform the conversion. However, it is not to say that the conversion can not be performed by a device other than the controller related to the irradiation device (for example, the treatment plan device). In Embodiment 2, there is shown a situation where the conversion to the command value is performed by an external device.

Figure 4:
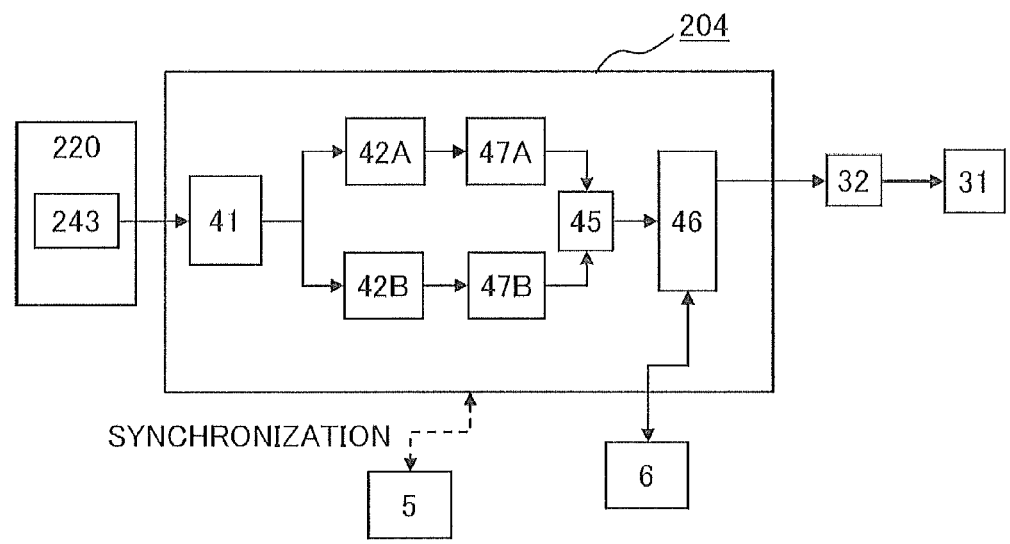
FIG. 4 is a block diagram for illustrating a control device for scanning electromagnet in a particle beam therapy apparatus according to Embodiment 2 of the invention.

FIG. 4 is a block diagram for illustrating a configuration of a controller (control unit) for scanning electromagnet in a particle beam therapy apparatus according to Embodiment 2 of the invention. As shown in FIG. 4, in a treatment plan device 220, there is included an arithmetic circuit 243 that performs calculation for converting the treatment plan data to the command value. Besides, in a controller 204 for the irradiation device 3, an interface 41 receives the command value instead of the treatment plan data, and a memory stores the command value received by the interface 41. Here, in Embodiment 2, the memory 42 is made redundant to be arranged in two lines with two memories of a memory 42A and a memory 42B. Further, in the respective lines, there is provided a timing adjustment circuit 47 that is made redundant (47A, 47B) and that functions as a timing adjustment unit for outputting the command value stored in the memory while adjusting its timing (in synchronization with the accelerator-related control unit 5). Namely, in the command-value processing line, the memory and the timing adjustment circuit are made redundant. Then, each command value output from each redundant command-value processing line is output to the comparator unit 45, and thereafter, the same operation with the same configuration as in Embodiment 1 is performed.

Namely, a difference from Embodiment 1 resides firstly in that the conversion from the treatment plan data to the command value is performed by a device other than the control unit 204 (as shown in the figure, for example, by the treatment plan device 220). Thus, the command value processing line in the control unit 204 does not perform calculation for the conversion to the command value, and its function is limited to only outputting the signal in synchronization with the control unit 5 related to the accelerator. Another difference from Embodiment 1 resides in providing the memory also formed in two lines. This is because it has been found that a failure of the controller related to the irradiation device occurs in the memory more frequently than in a portion that mainly takes the calculation or the timing. Thus, there is provided the memory also formed in two lines. Note that, although the calculation up to the command value is physically executed by the treatment plan device 220, it may be regarded that a part of function of the control unit 204 for the scanning electromagnet 31 is placed in the treatment plan device 220.

As describe above, according to the control device for scanning electromagnet (control unit 204) according to Embodiment 2, there is provided a control device for scanning electromagnet (control unit 204) to be used for controlling the scanning electromagnet 31 that is used for scanning irradiation so as to form the particle beam supplied from the accelerator 10 into an irradiation field matched to a treatment plan, said control device for scanning electromagnet being configured to include: the arithmetic circuit 243, the memory 42 and the timing adjustment circuit 47 that function as a command-value processing unit that generates a command value for driving the scanning electromagnet 31 on the basis of the treatment plan (or its data), and outputs the generated command value in synchronization with the accelerator 10; and the error detection unit (comparator unit 45) that detects a processing error in the command-value processing unit; wherein a circuit (memory 42 and timing adjustment circuit 47) that constitutes at least a part of the command-value processing unit is made redundant (as memories 42A, 42B and timing adjustment circuits 47A, 47B), and the error detection unit (comparator unit 45) detects occurrence of the processing error when outputs from the circuit made redundant are unmatched to each other. Thus, when an error occurred in the command value processing, it is possible to detect it promptly. This makes it possible to suppress an excessive dose from occurring, for example, due to concentration of dose caused by the irradiation position staying unchanged or due to false radiation to a site that should never be irradiated, to thereby perform a particle beam therapy that is capable of imparting an optimum dose.

In particular, as redundant circuits, the memories 42A, 42B are provided that retain the generated command values, so that an error due to failure of the easily-influenced memory in the processing of generating the command value can be promptly detected.

Further, as redundant circuits, the timing adjustment circuits 47A, 47B are provided that output the generated command values in synchronization with the accelerator 10, so that a processing error, such as a stagnation in outputting the command value, a timing error, etc., can be promptly detected.

Further, according to the particle beam therapy apparatus 1 according to Embodiment 2, it is configured to include: the accelerator 10 that supplies a particle beam; the irradiation device 3 that includes the scanning electromagnet 31 for performing scanning and performs scanning irradiation matched to a shape of a diseased site using the particle beam supplied from the accelerator 10; the above-described control device for scanning electromagnet (control unit 204) that controls the scanning electromagnet 31; and the cooperation control device (control unit 6) that controls the accelerator 10 and the irradiation device 3 in their cooperative manner; wherein, when the error detection unit (comparator unit 45) detects a processing error, the control device for scanning electromagnet (control unit 204) outputs an error-occurrence signal indicative of occurrence of the processing error to the cooperation control device (control device 6); and wherein, when the error-occurrence signal is output, the cooperation control device (control device 6) suspends at least one of the supply of the particle beam by the accelerator 10 and the irradiation with the particle beam by the irradiation device 3. Thus, it is possible to suppress an excessive dose from occurring due to concentration of dose caused by the irradiation position staying unchanged or due to false radiation to a site that should never be irradiated, to thereby perform a particle beam therapy that is capable of imparting an optimum dose.

Embodiment 3

In Embodiments 1 and 2, the error detection unit (comparator unit 45) and an error notification means (interface 46) are both included in the controller for the irradiation device (control unit 4, 204). In these cases, it is unable to take a measure against a trouble caused by noise or the like that is carried on the signal line through which the command value is transmitted from the control unit 4 to the scanning electromagnet 31 (or driving power source 32). Depending on the situation, there is a demand that the comparison in command-value processing is to be performed as much as possible at the periphery. Thus, in the particle beam therapy apparatus according to Embodiment 3, the error detection means and the error notification means are placed in the driving power source for the scanning electromagnet as a part other than the controller for the irradiation device.

Figure 5:
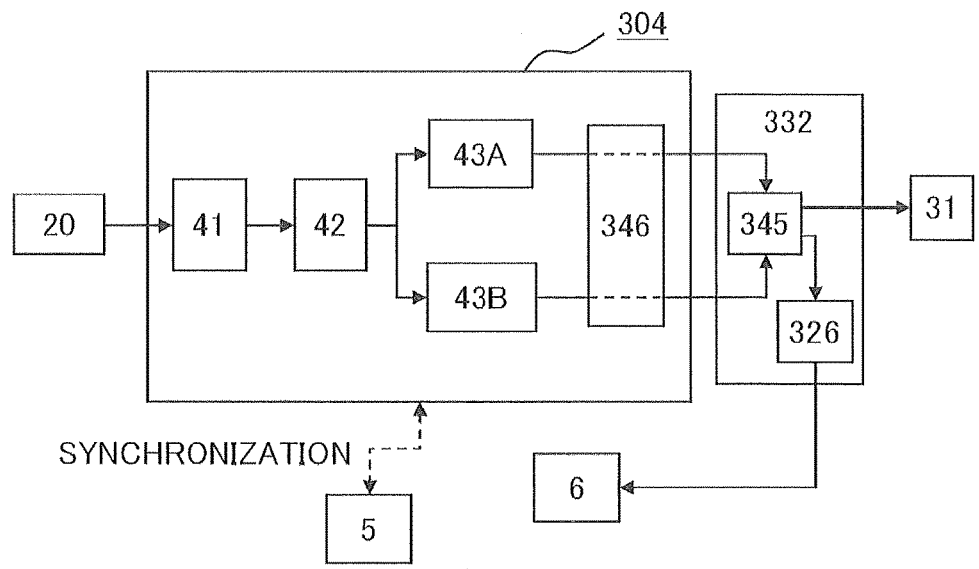
FIG. 5 is a block diagram for illustrating a control device for scanning electromagnet in a particle beam therapy apparatus according to Embodiment 3 of the invention.

FIG. 5 is a block diagram showing a configuration of a controller (control unit) for controlling an irradiation device in the particle beam therapy apparatus according to Embodiment 3 of the invention. As shown in FIG. 5, a comparator unit 345 that functions as an error detection means, and an error output unit 326 that functions as an error notification means are placed in a driving power source 332 for the scanning electromagnet 31.

As shown in FIG. 5, a control unit 304 is provided with an interface 41, a memory 42 and redundant first arithmetic circuit 43A and second arithmetic circuit 43B, the configuration of which is similar to the configuration illustrated in FIG. 3 of Embodiment 1. However, the control unit does not have the comparator unit 45 therein, and its interface 346 has no function as an error notification means. Thus, the command values calculated by the first arithmetic circuit 43A and the second arithmetic circuit 43B are output without change to the driving power source 332 through the interface 346.

The comparator unit 345 and the error output unit 326 are provided in the driving power source 332. Then, the command value from the first arithmetic circuit 43A and the command value from the second arithmetic circuit 43B that have been output to the driving power source 332 through the interface 346, are output to the comparator unit 345, respectively. As similar to the comparator unit 45 in Embodiment 1 or 2, the comparator unit 345 compares both of the command values. Then, when both of the compared command values are matched to each other, the command value is output to the scanning electromagnet 31, and when both of the command values are unmatched to each other, an error-occurrence trigger signal is output to the error output unit 326. When the error-occurrence trigger signal is output, the error output unit 326 outputs the error-occurrence trigger signal to the main control unit 6.

By providing the thus-described configuration, it is possible to exhibit such an effect that allows to take a measure, such as the suspension etc., by detecting an error related to the command value, even when noise or the like is carried on the signal line for transmitting the command value within its portion from the control unit 304 up to the driving power source 332.

As described above, according to the control device for scanning electromagnet (control unit 304; comparator unit 345 in driving power source 332) according to Embodiment 3, it is configured so that the error detection unit (comparator unit 345) is placed in the driving power source 332 for driving the scanning electromagnet 31. Thus, even when noise or the like is carried on the portion within from the control unit 304 up to the driving power source 332, it is possible to take a measure, such as the suspension etc., by detecting an error related to the Command value.

Further, according to the particle beam therapy apparatus 1 according to Embodiment 3, it is configured to include: the accelerator 10 that supplies a particle beam; the irradiation device 3 that includes the scanning electromagnet 31 for performing scanning and performs scanning irradiation matched to a shape of a diseased site using the particle beam supplied from the accelerator 10; the above-described control device for scanning electromagnet (control unit 304; comparator unit 345 in driving power source 332) that controls the scanning electromagnet 31; and the cooperation control device (control unit 6) that controls the accelerator 10 and the irradiation device 3 in their cooperative manner; wherein, when the error detection unit (comparator unit 345) detects a processing error, the control device for scanning electromagnet (control unit 304; comparator unit 345 and error output unit 326 in driving power supply 332) outputs an error-occurrence signal indicative of occurrence of the processing error to the cooperation control device (control unit 6); and wherein, when the error-occurrence signal is output, the cooperation control device (control unit 6) suspends at least one of the supply of the particle beam by the accelerator 10 and the irradiation with the particle beam by the irradiation device 3. Thus, it is possible to suppress an excessive dose from occurring due to concentration of dose caused by the irradiation position staying unchanged or due to false radiation to a site that should never be irradiated, to thereby perform a particle beam therapy that is capable of imparting an optimum dose.

Embodiment 4

In the above respective embodiments, description has been made to the cases where the most simple two redundant lines are given as a configuration of the command-value processing line that is made redundant for detecting an error occurred therein. However, the redundancy number is not necessarily limited to two, and may be three or more. If this is the case, a majority decision as disclosed in Patent Document 6 or 7 may be employed. In Embodiment 4, while the above-described majority decision is employed with the redundancy number set to be three or more, here is additionally specified an operation at the time of error detection as a result of focusing on a phenomenon unique to the particle beam therapy apparatus.

Figure 6:
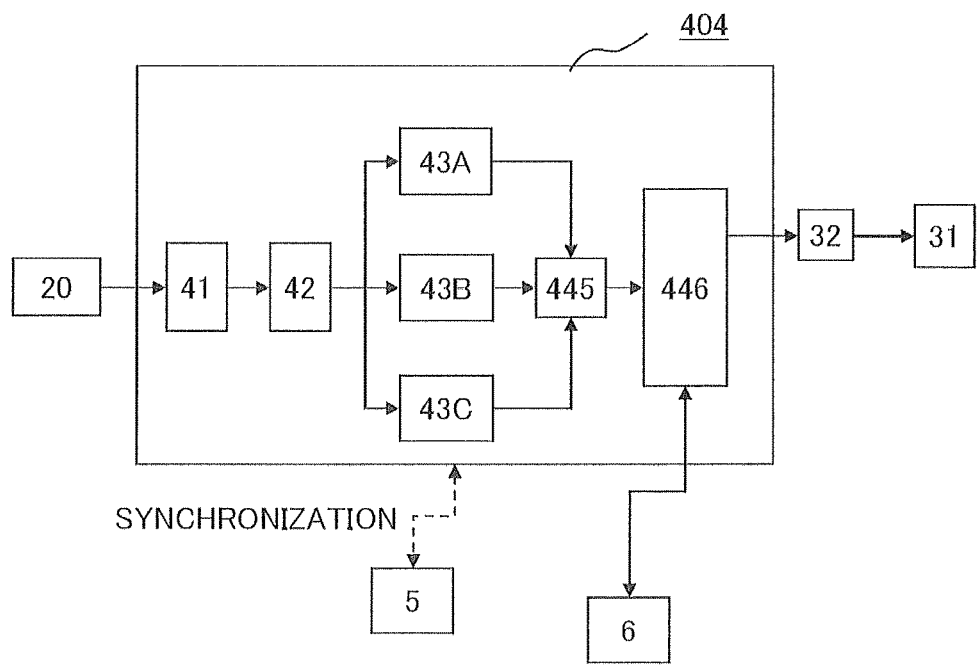
FIG. 6 is a block diagram for illustrating a control device for scanning electromagnet in a particle beam therapy apparatus according to Embodiment 4 of the invention.
Figure 7A:
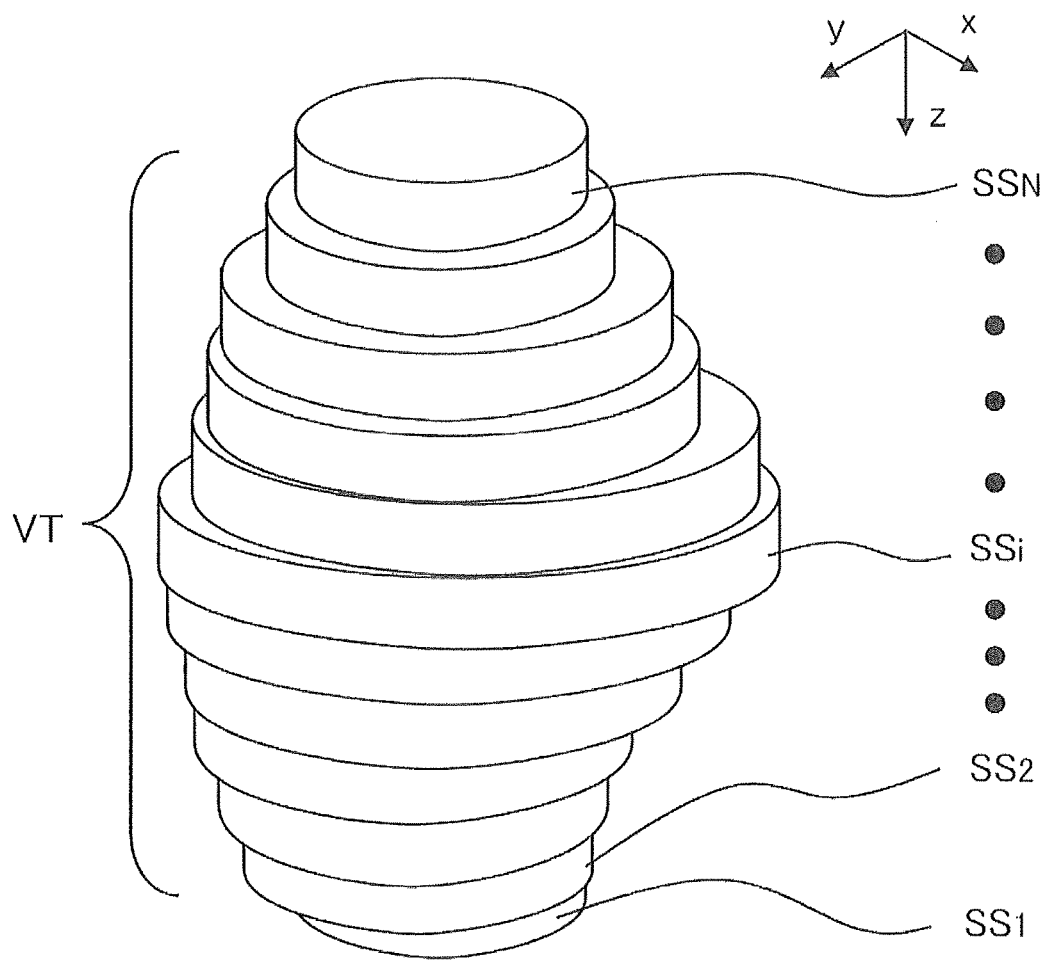
FIG. 7A and FIG. 7B are schematic diagrams for illustrating scanning irradiation made for every slice by the particle beam therapy apparatus according to Embodiment 4 of the invention.
Figure 7B:
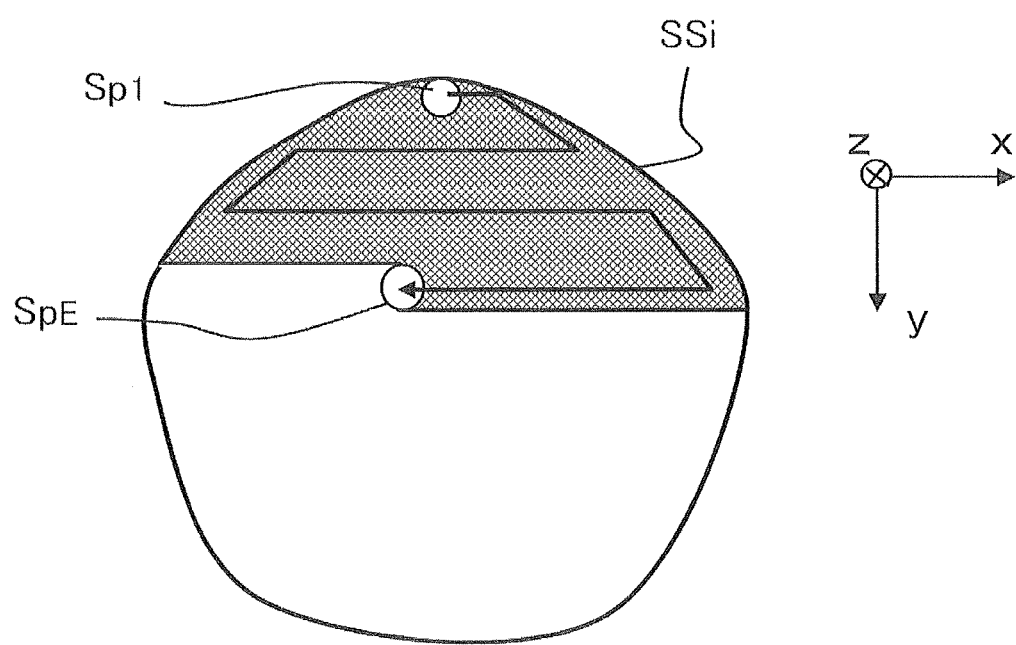
Figure 8:
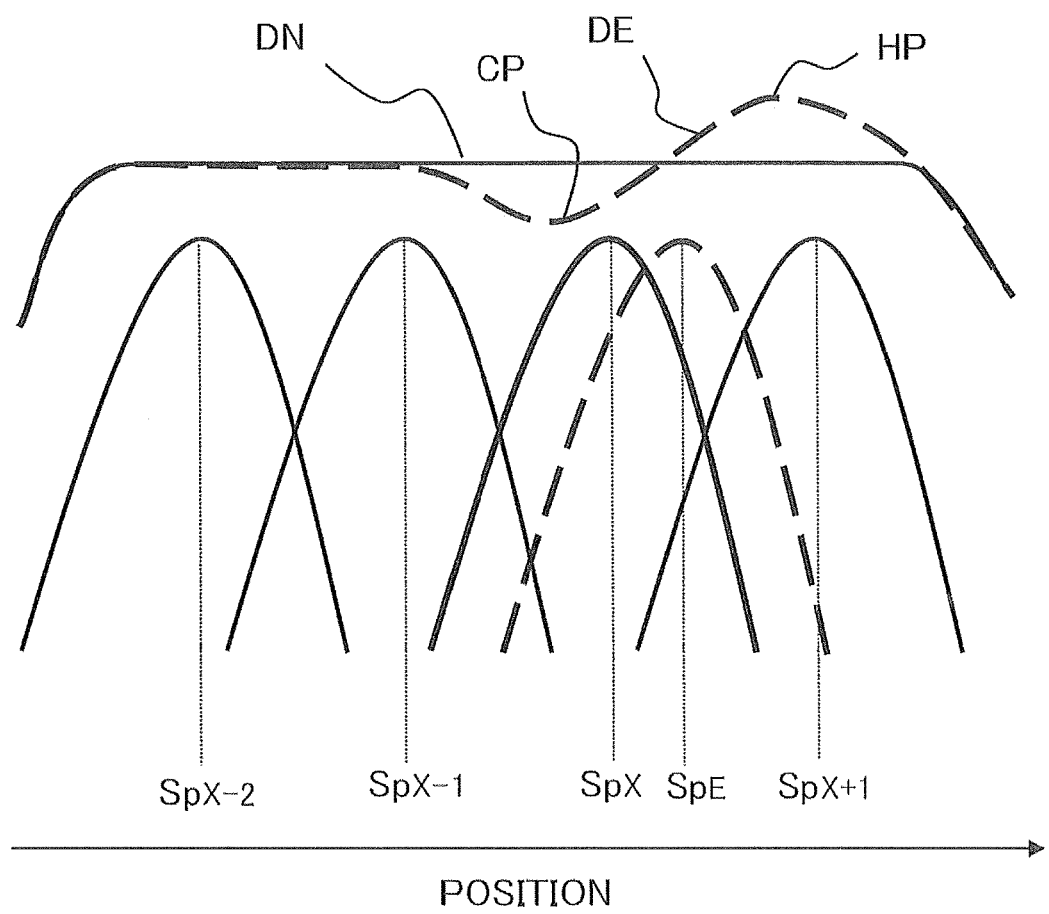
FIG. 8 is a diagram for illustrating a dose distribution in scanning irradiation in the case where a spot position is displaced.
Figure 9:
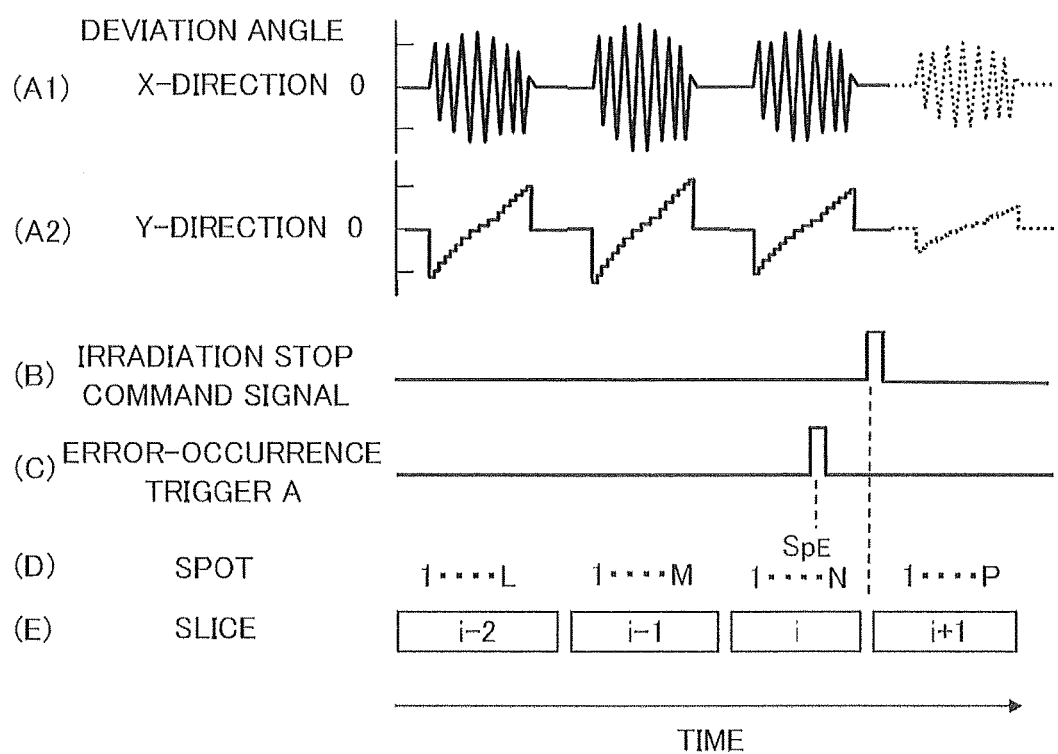
FIG. 9 is a waveform chart for illustrating an operation of the particle beam therapy apparatus according to Embodiment 4 of the invention.
Figure 10:
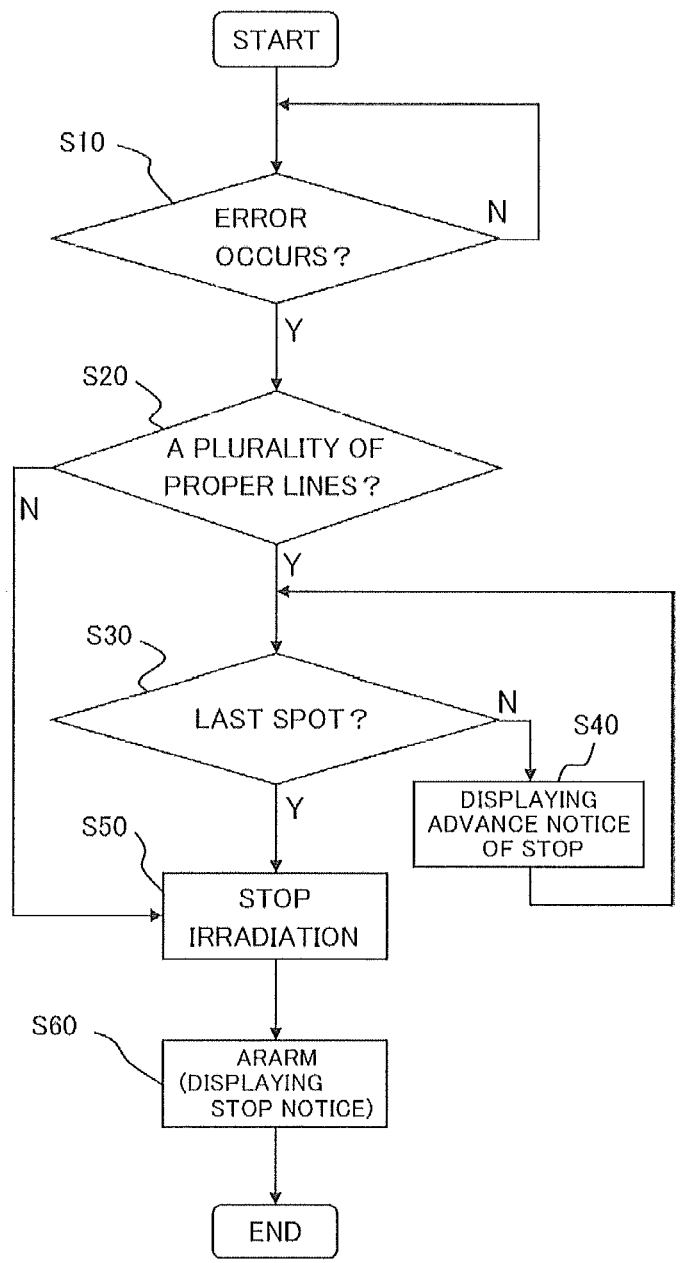
FIG. 10 is a flowchart for illustrating an operation of the particle beam therapy apparatus according to Embodiment 4 of the invention.

FIG. 6 to FIG. 10 are given for illustrating a configuration and an operation of the particle beam therapy apparatus according to Embodiment 4 of the invention, in which FIG. 6 is a block diagram showing a configuration of a control unit for irradiation device in the particle beam therapy apparatus, and FIG. 7 is schematic diagrams for illustrating layer-stacking conformal irradiation using scanning irradiation which includes an image of layer-stacking conformal irradiation (FIG. 7A) and a schematic diagram showing scanning in a slice (FIG. 7B). FIG. 8 is a diagram for illustrating a dose distribution in scanning irradiation in the case where a spot position is displaced, in which shown are one dimensional dose distributions at the individual spots and their overlapping dose distribution. Further, FIG. 9 is a waveform chart for illustrating an operation of the particle beam therapy apparatus according to Embodiment of the invention, and FIG. 10 is a flowchart for illustrating an operation of the particle beam therapy apparatus according to Embodiment 4 of the invention.

It is noted that, as shown in FIG. 6, in a control unit 404 for the scanning electromagnet 31 in the particle beam therapy apparatus 1 according to Embodiment 4, there is provided an arithmetic circuit 43 that performs calculation for converting the treatment plan data to the command value for the scanning electromagnet 31 (or its driving power source 32), said arithmetic circuit being made redundant as three circuits of a first arithmetic circuit 43A, a second arithmetic circuit 43B and a third arithmetic circuit 43C each executing the same calculation.

The respective command values calculated by the redundant first arithmetic circuit 43A, second arithmetic circuit 43B, and third arithmetic circuit 43C are output to a comparator unit 445. The comparator unit 445 compares the command values output from the three arithmetic circuits (command-value processing lines) to each other. Then, in the case where the thus-compared three command values are matched to each other, the command value is output to an interface 446. In contrast, in the case where there is an unmatched command value, a corresponding error-occurrence trigger is output that is depending on the number of matched command values. When there is command values matched to each other even if one of the command values is unmatched (there is two or more same command values), the matched command value and an error-occurrence trigger A as a signal indicative of a slight error are output to the interface 446. In contrast, when there is no matched command value at all, an error-occurrence trigger B as a signal indicative of a serious error is output to the interface 446. Namely, the error detection means (comparator unit 445) according to Embodiment 4 judges not only whether an error occurred or not in any one of the redundant command-value processing lines, but also the degree (seriousness) of the occurred error.

When the command value is output to the interface 446, the interface 446 outputs the command value to the driving power source 32, and the driving power source 32 drives the scanning electromagnet 31 on the basis of the output command value. On the other hand, when the error-occurrence trigger signal A and the command value are output to the interface 446, the interface 446 outputs the error-occurrence trigger signal A to the main control unit 6. Alternatively, when the error-occurrence trigger signal B is output to the interface 446, the interface 446 outputs the error-occurrence trigger signal B to the main control unit 6.

Then, when the output signal is the error-occurrence trigger signal B, similarly to the above-described respective embodiments, the main control unit 6 indicates the error and provides an output for suspending the particle beam to the corresponding controllers (for example, controllers 404, 5, etc.). However, when the error-occurrence trigger signal A indicative of a slight error is output, the main controller controls the corresponding controllers (for example, controllers 404, 5, etc.) so that the particle beam is suspended after completion of irradiation of that slice. In the followings, the background of employing such a configuration and details of operation thereof will be described.

First, description will be made about the layer-stacking conformal irradiation. In a layer-stacking conformal irradiation method, as shown in FIG. 7A, a tridimensional shape of the diseased site T is partitioned in depth direction from the body surface into a plurality of layers having predetermined thicknesses (slice $SS_1$, $SS_2$, . . . $SS_N$). Then, every partitioned slice is individually irradiated in such a manner that its shape in planar direction (x-y) is fully covered. On this occasion, when an irradiation field in planar direction is to be formed by scanning irradiation, an area in planar direction of the slice is scanned by a small spot so that the area is fully covered. For example, in FIG. 7B, there is shown an example in which the area in planar direction of the slice $SS_i$ is fully covered by being scanned in a zig-zag manner starting from a spot $Sp_i$. Note that the scanning route in scanning irradiation is not limited to be in a zig-zag form as shown in the figure, and spiral or like various forms can be applied thereto.

In the example as shown in FIG. 7, the specification of the ridge filter 33 is adjusted so that SOBP matched to a depth of each slice SS is established. Further, at the stating of irradiation, the energy of the particle beam supplied to the irradiation device 3 and the specification of the range shifter 34 are adjusted so that a range corresponding to the depth of the slice $SS_1$ at the deepest portion is established, followed by execution of scanning irradiation for the slice $SS_1$. Then, after completion of irradiation of the slice $SS_1$ at the deepest portion, the range is adjusted automatically by the range shifter 34 to a position shallower (a near side viewed from the irradiation device 3) by a depth corresponding to SOBP, followed by execution of scanning irradiation for the next slice $SS_2$. Thereafter, while adjusting the range similarly by the range shifter 34, irradiation is made and completed for slices up to the final slice $SS_N$, which results in dose impartation to a space VT corresponding to the whole tridimensional shape of the diseased site T.

At this time, dose impartation in a plane of each slice $SS_i$ is achieved by scanning a narrow particle beam, such as a pencil beam; however, the dose distribution at each one spot is uneven within the spot diameter and has a Gaussian distribution as shown in FIG. 8. Thus, by placing the positions of respective spots ($Sp_{X-2}$, $Sp_{X-1}$, $SP_X$, $Sp_{X+1}$) with calculated intervals therebetween, it is possible to achieve a dose distribution DN that is even in the plane as a whole. Here, for example, when the spot $Sp_X$ is positionally displaced to a spot $Sp_E$, because the interval between the spots $Sp_{X-1}$ and $Sp_E$ becomes broader than is expected, a cold point CP emerges where the dose is lower than is planned, and because the interval between the spots $Sp_E$ and $Sp_{X+1}$ becomes narrower than is expected, a hot point HP emerges where the dose is higher than is planned. Namely, there is provided a dose distribution DE having a deviation in the plane.

Although such a hot point or a cold point is classified depending on its degree to a therapeutically acceptable or unacceptable one, what is generally made acceptable is in the case where the positional accuracy of the spot falls within 5% of the standard deviation "σ" in the distribution of the particle beam. Here, for example, when "σ" in the dose distribution by the particle beam in scanning irradiation is assumed to be about 3 mm, the positional accuracy to be required falls within 0.15 mm. On the other hand, the position-determining accuracy of the patient on the treatment table, etc., is targeted to be ±0.3 mm, so that the actual position-determining accuracy becomes rougher than the positional accuracy of the spot.

It is noted that the position-determining accuracy is useful for matching the position of patient to the irradiation region, and if the position falls within that accuracy at the time of starting the treatment, there is no difficulty to impart dose just according to the treatment plan. However, when the position of patient is changed during irradiation of one slice, even if the position is matched to within that accuracy, a hot spot or a cold spot emerges that exceeds the acceptable level. In other words, once irradiation of the slice has been started, when the irradiation of the slice is stopped at an intermediate spot, it is found difficult to impart dose just according to the treatment plan even if getting a fresh start of irradiation from that spot.

Thus, the particle beam therapy apparatus according to Embodiment 4 is configured so that, even in the case of occurrence of an error in the command value, if the command values are matched to each other at least at a plurality of lines among the redundant command-value processing lines, irradiation is continued until irradiation of that slice is completed. This makes it possible to impart dose uniformly in that slice unless otherwise a vital error occurs (all command values are unmatched). However, this does not mean that an even distribution is optimum, but means that in an easily-explainable case where an even distribution is set in the treatment plan, the distribution is achieved just according to that setting. Accordingly, by using the particle beam therapy apparatus according to this embodiment, when a deviated dose distribution has been set under the treatment plan, it becomes possible to impart dose just according to that distribution having been set.

Next, the operation will be described using the waveform chart in FIG. 9 and the flowchart in FIG. 10.

In FIG. 9, there are shown waveforms in irradiation periods of given four successive slices ($SS_{i-2}$, $SS_{i-1}$, $SS_i$, $SS_{i+1}$) in layer-stacking conformal irradiation having been described using FIG. 7. Here, such a case is assumed where an area in each slice SS is fully covered by being scanned along one direction i.e. the y-direction while being scanned in the x-direction in a zig-zag manner, and an error is detected during irradiation of the slice $SS_i$. In the figure, shown at (A1) and (A2) are bending angles (angles that the particle beam is deviated by at the time a current just according to the command value flows) that are set for the unidirectional scanning electromagnets 31a and 31b, respectively; shown at (B) is an irradiation stop command signal; at (C) is an error-occurrence trigger A; at (D) are spots; and at (E) are slices.

After starting irradiation, in the slices $SS_{i-2}$ and $SS_{i-1}$, no error occurs (in Step S10, "N") and currents according to the set command values flow through the unidirectional scanning electromagnets 31a,31b of the scanning electromagnet 31, respectively, so that the bending angles of the particle beam are changed depending on time to thereby execute scanning irradiation. Further, even in the slice $SS_i$, before the spot $Sp_E$, no error occurs and scanning irradiation is executed.

Here, during irradiation of the spot $Sp_E$, if at least one command value is unmatched among the command values output from the three command-value processing lines, the comparator unit 445 detects occurrence of an error (in Step S10, "Y"). Then, the flow moves to Step S20 and it is determined whether or not there are lines that output the same command values (Step S20). If there are lines that output the same command values, it is determined that the line is proper and there are a plurality of proper lines (in Step S20, "Y").

In this case, the comparator unit 445 transmits the command value determined to be proper, together with the error-occurrence trigger A, to the interface 446. The interface 446 outputs the command value to the driving power source 32, and also outputs the error-occurrence trigger A to the main control unit 6. Then, when the spot at the time of occurrence of the error is not the last spot in that slice (in Step S30, "N"), the main control unit 6 only outputs a command to the corresponding controllers for causing them to execute displaying an advance notice of stop of irradiation due to occurrence of the error. Then, when reaching to the last spot of that slice (in Step S30, "Y"), the main controller stops the irradiation with the particle beam (Step S50) and outputs the irradiation stop command signal to the corresponding controllers for causing them to execute displaying a stop notice (Step S60).

As a result, irradiation is completed up to the slice $SS_i$, and the irradiation is stopped. Note that the irradiation stop command is not necessarily required to be output at the timing of reaching to the last spot of that slice, and may be output at any timing where irradiation with the particle beam can be suspended promptly after the time of reaching to the last spot of that slice.

On the other hand, if it is determined in Step S20 that there is no line at all that outputs the same command value, the comparator unit 445 transmits the error-occurrence trigger B to the interface 446, and the interface 446 having received the error-occurrence trigger B outputs the error-occurrence trigger B to the main control unit 6. Then, the main control unit 6 promptly stops the irradiation with the particle beam (Step S50), and also outputs the irradiation stop command signal to the corresponding controllers for causing them to execute displaying a stop notice (Step 360).

It is noted that, even in a case that has been determined as "Y" in Step S20 and thus corresponds to the sequence in which the irradiation is continued to the last of that slice, if the command value becomes unmatched to the command values of the other two lines, the flow moves to an immediately-suspending operation.

It is further noted that, as a matter of course, a target to be made redundant into three or more numbers, a modification in physical arrangement of the circuits, and the like, may be appropriately determined by combining examples in the respective embodiments described above.

As described above, according to the control device for scanning electromagnet (control unit 404) according to Embodiment 4, there is provided a control device for scanning electromagnet (control unit 404) to be used for controlling the scanning electromagnet 31 that is used for scanning irradiation so as to form the particle beam supplied from the accelerator 10 into an irradiation field matched to a treatment plan, said control device for scanning electromagnet being configured to include: the memory 42, the arithmetic circuit 43 and the interface 446 that function as a command-value processing unit that generates a command value for driving the scanning electromagnet 31 on the basis of the treatment plan (or its data), and outputs the generated command value in synchronization with the accelerator 10; and the error detection unit (comparator unit 445) that detects a processing error in the command-value processing unit; wherein a circuit (arithmetic circuit 43) that constitutes at least a part of the command-value processing unit has three or more circuits (arithmetic circuits 43A, 43B, 43C), and the error detection unit (comparator unit 445) detects occurrence of the processing error when outputs from such redundant circuits are unmatched to each other, and determines the degree of the occurred error depending on the number of the circuits whose outputs are matched to each other among the three or more circuits. Thus, when an error occurred in the command value processing, it is possible to detect it promptly, as well as to take appropriate processing depending on the degree of the error. This makes it possible to suppress an excessive dose from occurring, for example, due to concentration of dose caused by the irradiation position staying unchanged or due to false radiation to a site that should never be irradiated, as well as to minimize a harmful effect, for example, due to an interruption of irradiation or the like, to thereby perform a particle beam therapy that is capable of imparting an optimum dose.

Further, according to the particle beam therapy apparatus 1 according to Embodiment 4, it is configured to include: the accelerator 10 that supplies a particle beam; the irradiation device 3 that includes the range shifter 34 and the ridge filter 33 that functions as a range adjustment device for adjusting the range of the particle beam, and the scanning electromagnet 31 for scanning irradiation and performs irradiation matched to the tridimensional shape of the diseased site by scanning irradiation for every slice SS (layer-stacking conformal irradiation) using the particle beam supplied from the accelerator 10; the above-described control device for scanning electromagnet (control unit 404) that controls the scanning electromagnet 31; and the cooperation control device (control unit 6) that controls the accelerator 10 and the irradiation device 3 in their cooperative manner; wherein, when the error detection unit (comparator unit 445) detects a processing error, the control device for scanning electromagnet (control unit 404) outputs an error-occurrence signal indicative of occurrence of the processing error and the degree of the occurred error to the cooperation control device (control device 6); and wherein, when the error-occurrence signal having been output indicates that the degree of the error is high (error-occurrence trigger signal B), the cooperation control device (control device 6) immediately suspends at least one of the supply of the particle beam by the accelerator 10 and the irradiation with the particle beam by the irradiation device 3, and when the error-occurrence signal indicates that the degree of the error is not high (error-occurrence trigger signal A), the cooperation control device, after completion of irradiation of the slice SS at the time of occurrence of the error, suspends at least one of the supply of the particle beam by the accelerator 10 and the irradiation with the particle beam by the irradiation device 3. Thus, it is possible to suppress an excessive dose from occurring, for example, due to concentration of dose caused by the irradiation position staying unchanged or due to false radiation to a site that should never be irradiated, as well as to minimize a harmful effect, such as occurrence of a hot spot or a cold spot, for example, due to a displacement in set position of the patient caused by an interruption of irradiation in the slice, to thereby perform a particle beam therapy that is capable of imparting an optimum dose.

DESCRIPTION OF REFERENCE NUMERALS AND SIGNS

1: particle beam therapy device,
3: irradiation device,
4: local control unit (control device for scanning electromagnet),
5: local control unit (control unit for accelerator),
6: main control unit (cooperation control device),
10: accelerator,
31: scanning electromagnet,
32: driving power source,
41: interface,
42: memory,
43: arithmetic circuit,
45: comparator unit (error detection unit),
47, 326: timing adjustment circuit.
NOTE: A digit in the hundred's place represents a modification example corresponding to each embodiment.

The invention claimed is:
1. A control device for scanning electromagnet to be used for controlling a scanning electromagnet that is used for scanning irradiation so as to form a particle beam supplied from an accelerator into an irradiation field matched to a treatment plan, said control device for scanning electromagnet being placed under an environment where neutrons are produced and comprising:
   a command-value processing unit that generates a command value for driving the scanning electromagnet on a basis of the treatment plan, and outputs the generated command value in synchronization with the accelerator; and
   an error detection unit that detects a processing error in the command-value processing unit;
   wherein a circuit that constitutes at least a part of the command-value processing unit is made redundant, and the error detection unit detects occurrence of the processing error when outputs from the circuit made redundant are unmatched to each other.

2. The control device for scanning electromagnet according to claim 1, wherein the circuit made redundant is an arithmetic circuit that converts data of the treatment plan to the command value.

3. The control device for scanning electromagnet according to claim 2, wherein the circuit made redundant is a memory that retains the generated command value.

4. The control device for scanning electromagnet according to claim 3, wherein the circuit made redundant is a timing adjustment circuit that causes output of the generated command value to be output in synchronization with the accelerator.

5. The control device for scanning electromagnet according to claim 2, wherein the circuit made redundant is a timing adjustment circuit that causes output of the generated command value to be output in synchronization with the accelerator.

6. The control device for scanning electromagnet according to claim 2, wherein the error detection unit is placed in a driving power source for driving the scanning electromagnet.

7. The control device for scanning electromagnet according to claim 2, wherein the circuit made redundant includes three or more circuits, and the error detection unit, when detected occurrence of the processing error, determines a degree of the occurred error according to a number of circuits whose outputs are matched to each other among the three or more circuits.

8. A particle beam therapy apparatus, comprising:
an accelerator that supplies a particle beam;
an irradiation device that includes a range adjustment device that adjusts a range of the particle beam and a scanning electromagnet used for scanning irradiation, and performs irradiation matched to a tridimensional shape of a deceased site by scanning irradiation for each of slices using the particle beam supplied from the accelerator;
the control device for scanning electromagnet according to claim 7, that controls the scanning electromagnet; and
a cooperation control device that controls the accelerator and the irradiation device in their cooperative manner;
wherein, when the error detection unit detects the processing error, the control device for scanning electromagnet outputs an error-occurrence signal indicative of occurrence of the processing error and the degree of the occurred error, to the cooperation control device;
wherein, when the error-occurrence signal having been output indicates that the degree of the error is high, the cooperation control device immediately suspends at least one of the supply of the particle beam by the accelerator and the irradiation with the particle beam by the irradiation device, and
wherein, when the error-occurrence signal indicates that the degree of the error is not high, the cooperation control device, after completion of irradiation of the slice at the time of occurrence of the error, suspends at least one of the supply of the particle beam by the accelerator and the irradiation with the particle beam by the irradiation device.

9. A particle beam therapy apparatus, comprising:
an accelerator that supplies a particle beam;
an irradiation device that includes a scanning electromagnet used for scanning irradiation and performs scanning irradiation matched to a shape of a deceased site using the particle beam supplied from the accelerator;
the control device for scanning electromagnet according to claim 2, that controls the scanning electromagnet; and
a cooperation control device that controls the accelerator and the irradiation device in their cooperative manner;
wherein, when the error detection unit detects the processing error, the control device for scanning electromagnet outputs an error-occurrence signal indicative of occurrence of the processing error to the cooperation control device; and
wherein, when the error-occurrence signal is output, the cooperation control device suspends at least one of the supply of the particle beam by the accelerator and the irradiation with the particle beam by the irradiation device.

10. The control device for scanning electromagnet according to claim 1, wherein the circuit made redundant is a memory that retains the generated command value.

11. The control device for scanning electromagnet according to claim 10, wherein the circuit made redundant is a timing adjustment circuit that causes output of the generated command value to be output in synchronization with the accelerator.

12. The control device for scanning electromagnet according to claim 1, wherein the circuit made redundant is a timing adjustment circuit that causes output of the generated command value to be output in synchronization with the accelerator.

13. The control device for scanning electromagnet according to claim 1, wherein the error detection unit is placed in a driving power source for driving the scanning electromagnet.

14. The control device for scanning electromagnet according to claim 1, wherein the circuit made redundant includes three or more circuits, and the error detection unit, when detected occurrence of the processing error, determines a degree of the occurred error according to a number of circuits whose outputs are matched to each other among the three or more circuits.

15. A particle beam therapy apparatus, comprising:
an accelerator that supplies a particle beam;
an irradiation device that includes a range adjustment device that adjusts a range of the particle beam and a scanning electromagnet used for scanning irradiation, and performs irradiation matched to a tridimensional shape of a deceased site by scanning irradiation for each of slices using the particle beam supplied from the accelerator;
the control device for scanning electromagnet according to claim 14, that controls the scanning electromagnet; and
a cooperation control device that controls the accelerator and the irradiation device in their cooperative manner;
wherein, when the error detection unit detects the processing error, the control device for scanning electromagnet outputs an error-occurrence signal indicative of occurrence of the processing error and the degree of the occurred error, to the cooperation control device;
wherein, when the error-occurrence signal having been output indicates that the degree of the error is high, the cooperation control device immediately suspends at least one of the supply of the particle beam by the accelerator and the irradiation with the particle beam by the irradiation device, and
wherein, when the error-occurrence signal indicates that the degree of the error is not high, the cooperation control device, after completion of irradiation of the slice at the time of occurrence of the error, suspends at least one of the supply of the particle beam by the accelerator and the irradiation with the particle beam by the irradiation device.

16. A particle beam therapy apparatus, comprising:
an accelerator that supplies a particle beam;

an irradiation device that includes a scanning electromagnet used for scanning irradiation and performs scanning irradiation matched to a shape of a deceased site using the particle beam supplied from the accelerator;

the control device for scanning electromagnet according to claim 1, that controls the scanning electromagnet; and a cooperation control device that controls the accelerator and the irradiation device in their cooperative manner;

wherein, when the error detection unit detects the processing error, the control device for scanning electromagnet outputs an error-occurrence signal indicative of occurrence of the processing error to the cooperation control device; and wherein, when the error-occurrence signal is output, the cooperation control device suspends at least one of the supply of the particle beam by the accelerator and the irradiation with the particle beam by the irradiation device.

* * * * *